(12) United States Patent
Ben-David et al.

(10) Patent No.: US 12,016,365 B2
(45) Date of Patent: Jun. 25, 2024

(54) METHOD FOR FLAVOR PROFILE AND NUTRITION VALUES RETENTION OF CUSTOMIZED DISH RECIPE

(71) Applicant: Kitchen Robotics Ltd, Modiin (IL)

(72) Inventors: David Ben-David, Rehovot (IL); Yair Gordin, Modiin (IL)

(*) Notice: Subject to any disclaimer, the term of this patent is extended or adjusted under 35 U.S.C. 154(b) by 831 days.

(21) Appl. No.: 17/151,230

(22) Filed: Jan. 18, 2021

(65) Prior Publication Data

US 2022/0225657 A1 Jul. 21, 2022

(51) Int. Cl.
| | |
|---|---|
| *A23P 10/00* | (2016.01) |
| *A47J 43/00* | (2006.01) |
| *G01G 19/415* | (2006.01) |
| *G01N 33/02* | (2006.01) |
| *G06F 16/901* | (2019.01) |
| *G06F 16/9035* | (2019.01) |

(52) U.S. Cl.
CPC .............. *A23P 10/00* (2016.08); *A47J 43/00* (2013.01); *G01G 19/415* (2013.01); *G01N 33/02* (2013.01); *G06F 16/902* (2019.01); *G06F 16/9035* (2019.01)

(58) Field of Classification Search
CPC .... A23P 10/00; G06F 16/902; G06F 16/9035; A47J 43/00; G01G 19/415; G01N 33/02
See application file for complete search history.

(56) References Cited

U.S. PATENT DOCUMENTS

| | | | | |
|---|---|---|---|---|
| 9,414,623 | B2* | 8/2016 | Minvielle | A23P 10/00 |
| 9,702,858 | B1* | 7/2017 | Minvielle | A47J 36/321 |
| 9,902,511 | B2* | 2/2018 | Minvielle | A23P 10/00 |
| 2005/0287499 | A1* | 12/2005 | Yeager | G06Q 30/02 |
| | | | | 600/300 |
| 2007/0094090 | A1* | 4/2007 | Jenkins | G06Q 50/12 |
| | | | | 705/26.5 |
| 2009/0105875 | A1* | 4/2009 | Wiles | G07F 11/70 |
| | | | | 700/239 |
| 2019/0228855 | A1* | 7/2019 | Leifer | G06F 16/90324 |
| 2020/0159750 | A1* | 5/2020 | Shadrokh | G06V 10/25 |
| 2022/0225657 | A1* | 7/2022 | Ben-David | G06F 16/902 |

* cited by examiner

*Primary Examiner* — Omar Flores Sanchez
(74) *Attorney, Agent, or Firm* — M. Factor—1st-Tech-Ideas.com

(57) ABSTRACT

The present invention provides a method of retaining the dish flavor profile and nutrition values, of customized dish recipes. The dish recipe customization might result in adding or removing one or more ingredients, changing the amount of one or more ingredients of the originally defined recipe, and may also involve changing the recipe or a dish flavor profile. The method also derives and assigns a flavor profile to a specific customized recipe.

6 Claims, 1 Drawing Sheet

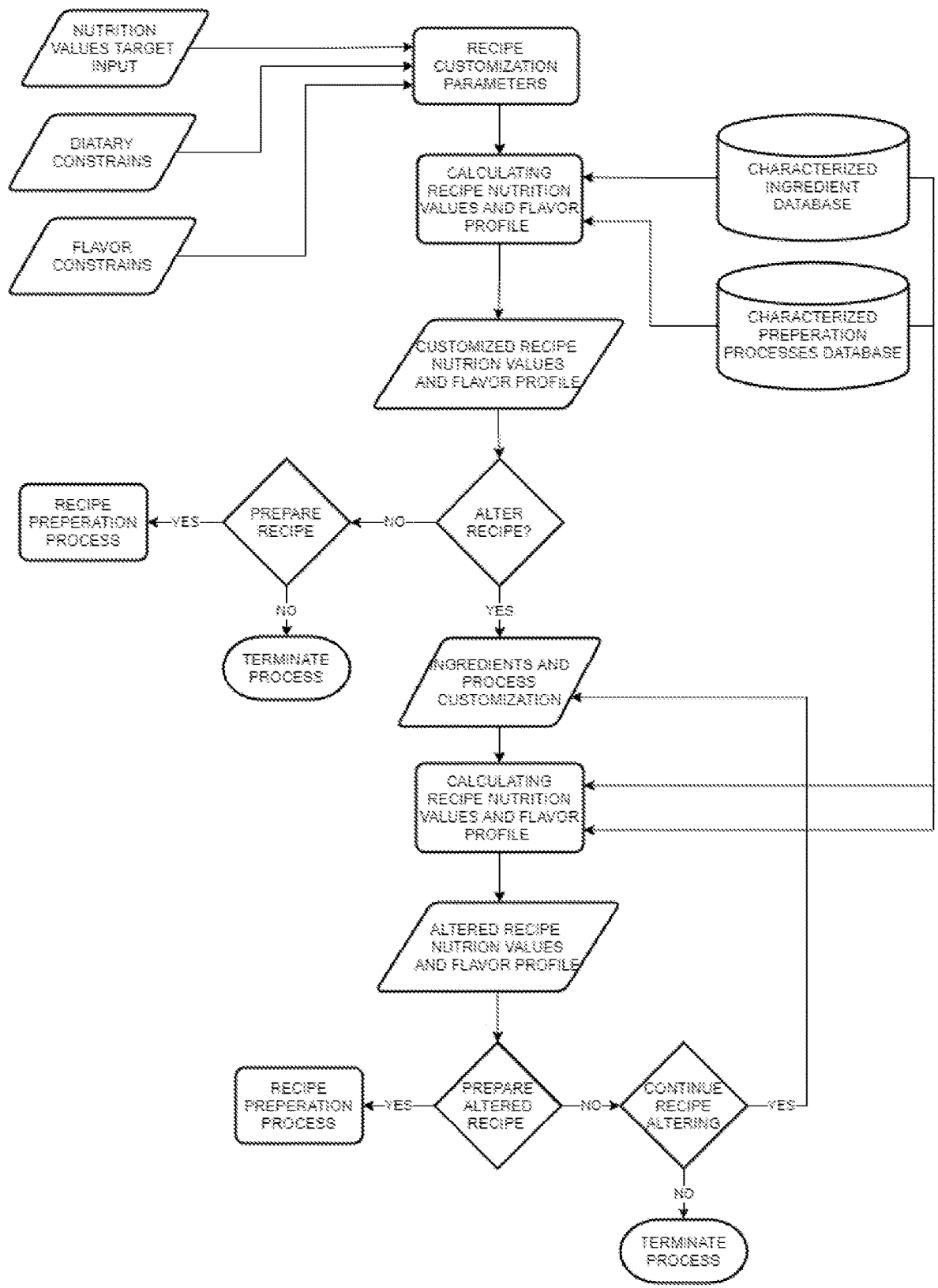

METHOD FOR FLAVOR PROFILE AND NUTRITION VALUES RETENTION OF CUSTOMIZED DISH RECIPE

A method for flavor profile and nutrition values retention of customized dish recipe.

FIELD OF THE INVENTION

The present invention relates to a dynamic or automated menu customization method, thereby inducing specific flavor and nutritional values, to a specific user/consumer. More particularly, the said method allows users or customers to alter ordered meal recipe, by adding ingredients, removing ingredient or changing their amount.

BACKGROUND OF THE INVENTION

In present times, increasing awareness entailed customization in various spheres of the society to rope in optimized benefits. In that line, customized food intake involving customized recipes for various foods recipes/dishes allowed complete satisfaction of a typical consumer. The customer then prepares each of the dishes described by the recipes and takes them home in separate packages to be cooked as needed. Further with hectic lifestyle engulfing every aspect of the society, wherein sparing time for cooking becomes scarce, ready-made food availability has generated substantial demand.

However, in general online ordering systems, the trend is uniformity in food preparation which as specified above is contrary to the customized recipe demand that consumers off-late are demanding for. To cater to the new demand assorted online food ordering systems and methods are currently provided for achieving an array of objectives. These systems introduce a high level of meal recipe customization, adjusting the meal to the consumer's food consumption limitations, health constraints or other requirements. Altering a predefined meal recipe provides a high level of personalization, however might have a significant impact on the outcome, in terms of taste, nutrition fact and even looks of the served dish.

Various inventions patented in that line are as below.

US20070094090A1 titled, "Customized food preparation apparatus and method" provide an improved method of preparing and selling an article of food from a retail establishment is disclosed. The method includes receiving an order from a customer where the order identifies ingredients and a quantity for the ingredients. The order also includes a preparation instruction for at least one of the ingredients. The quantity of each of the ingredients is gathered as a function of the order. The ingredients are prepared at the retail establishment as a function of the preparation instruction to provide a prepared food article. The prepared food article is packaged for available delivery to the customer. The method can also include consulting a list of potential ingredients corresponding to a diet plan and gathering the ingredients as a function of the order and the list. A nutritional value may be calculated for the prepared food article and communicated to the customer. The order may be received over an internet connection. The customer may specify particular ingredients as a function of the brand of the ingredients or of a growth or storage condition of the ingredients. An apparatus for enabling a retail customer to make a payment for a purchase from a third party using a financial card through an internet connection is also disclosed. Other apparatus and methods are also disclosed.

US20050287499A1 titled, "System and method for generating personalized meal plans" talks of a system for personalized meal planning is provided which includes a client device and a meal planning center configured to communicate with the client device and to receive a customer's information, including a weight designator, a gender designator, a goal designator, and an activity level designator. The meal planning center includes a storage device and a processing unit. The storage device is configured to store recipe template files having an ingredient designator and a plurality of recipe rule factors, which include a nutrient contribution value, a minimum ingredient value, and a maximum ingredient value. A plurality of recipe rule factors are each assigned to each ingredient designator. The processing unit is configured to determine a nutritional allowance based upon the customer information and to create a recipe that satisfies the nutritional allowance by using the recipe rule factors assigned to the ingredient. The meal planning center is further configured to transmit the recipe to the client device.

US20090105875A1 titled, "Dairy product and process" relates to a system for dispensing a customized serving. The system includes an ingredient storage module 12, an ingredient processing module 18, a serving dispenser 20, a user interface 24, and a formulation database containing an inventory of ingredients stored in the storage module 12 from which potential servings will be formulated. The system also includes a controller 22 that is operatively linked to the storage module 12, the processing module 18, the dispenser 20, the interface 24 and the database. The controller 22 is programmed: (a) to receive a serving selection from the user; (b) to determine, using the database, a serving recipe that best approximates the user's serving selection; (c) to present the serving recipe to the user via the interface 24, and (d) upon a command from the user, to actuate the processing module 18 to prepare, and the serving dispenser 20 to dispense, a serving prepared from the serving recipe.

While all the above inventions describe customized dish/recipe methods/systems, none of these discuss customization of recipes apart from that of both flavour and nutritional values. Such a modification of flavour and nutritional values as per requirement of specific consumers, entailed more flexibility in the produced dishes apart from its acceptability. The present invention devices a sustainable method and system in incorporating customized flavour and nutritional values in a plurality of customized dishes produced in an automated/robotic environment.

SUMMARY OF THE INVENTION

An aspect of the present invention is to provide a method of retaining the dish flavor profile and nutrition values, of customized dish recipes.

In an aspect of the invention dish recipe customization might result in adding or removing one or more ingredients, changing the amount of one or more ingredients of the originally defined recipe, changing the recipe or a dish flavor profile.

A further aspect of the invention is a method to derive and assign a flavor profile to a specific recipe.

An aspect of the invention allows characterization of the food ingredients thereby evaluating the effect on the flavor profile elements per weight portion. Cooking methods and parameters, such as but not limited to, temperature, moisture, heating method (induction heating, gas heating, conventional oven, microwave, air fryer) might be characterized as well, evaluating their effect on the flavor profile.

A still further aspect of the present invention is food ingredient characterization. Each food ingredient might be characterized by quantifying its culinary properties such as but limited to, umami, sweetness, bitterness, salinity, sourness, spiciness. The ingredients might be graded by methods or equipment such as, but not limited to, a comparison method, by measuring instruments, using international scales or taste sensitivity tests and evaluations.

The food ingredient characterization might include the food ingredient physical properties such as but not limited to freezing, melting and boiling points, specific heat capacity, thermal conductivity, thermal diffusivity, size and thickness, deformation, density and specific gravity, refractive index, viscosity moisture levels and texture. The food ingredient characteristics might also include quantification of its nutrition facts.

Another aspect of the invention is creating a data base, containing characterized food ingredients and cooking methods. The data base might contain similar food ingredients supplied from different vendors, thus having different characteristics and nutrition facts. The data base might contain custom ingredient mixtures, such as sauces, of spices, characterized and evaluated accordingly, setting custom ingredient nutrition facts and flavor characteristics.

A still further aspect of the invention is a method to retain customized recipe flavor profile. A method in the present invention analyses the flavor profile after the dish recipe customization, indicating the specific characterisation parameters that have been changed as a result.

Customizing the recipe is quantified or evaluated by the specific ingredient or group of ingredients beings customized, considering their characteristic parameters to determine the effect on the recipe flavor profile and nutrition facts data. The method in this invention will graphically display the increase in the sodium levels or the salinity levels accordingly.

Alternatively, the method in this invention might suggest adding an ingredient to the recipe or increasing an amount of an existing ingredient, to retain the flavor profile.

Another aspect of the invention is dynamic display of the dish recipe flavor profile during real time customization Yet another aspect of the invention is retention of the dish recipe flavor profile by adjustment of the cooking method or cooking parameters, following recipe customization.

BRIEF DESCRIPTION OF THE DRAWINGS

FIG. 1 is a flow chart showing the steps of a method for flavor profile and nutrition values retention of customized dish recipe.

DETAILED DESCRIPTION

The embodiments disclosed herein provide a detailed method for analyzing the effect of the recipe customization on the recipe flavor profile, graphically presenting it and suggesting modifications for balancing the flavor profile, such as alternative ingredient substitution, adjusting the amount of recipe ingredients and altering the cooking regime, in which each ingredient is individually customized to proportions, as demanded by a typical consumer. The single customized dish recipe might include foods or flavors, nutritional additives, or other pharmacologically active substances, as stipulated by the consumers.

The said dish recipe customization is ensured using the method as ensured through an application program, for computerized processing wherein, options for addition/deletion/modification of the ingredients to enable develop a typical recipe as a low-fat one or an extra sweet one or like-wise are accomplished. Further, the application program allows the user/consumer the option of removal/addition of specific ingredients/components of a typical recipe as for example, that of meat and substituting the same with vegetable substitute. Other examples may be demanding a specific recipe as a low-fat recipe, or extra sweet recipe. Another example of dish recipe customization would be removing onions from a salad dish. Yet another example of dish recipe customization would be removing chicken from an Asian cuisine dish and adding tofu instead. Yet another example of dish recipe customization would be reducing the amount or number of mushrooms in a pasta dish.

Accordingly, in one of the embodiments, various systems as reflected in the stated application program are employed in a sequential/parallel process in effectuating the desired flavor/nutritional modification of a typical recipe, effectuated through appropriate software to enable automatic representation and suggestions for balancing and optimization of the said flavor/nutritional value in a customized cooked recipe/dish.

The system further comprises of data base of ingredients, cooking methods, preparation methods (such as freezing, boiling, deep frying, air frying), characterized by the nutrition facts and flavor profile elements, such as salinity, sweetness, boiling temperature and freezing temperature. Thus, the system in line includes a first database, containing characterized food ingredients and cooking methods. The data base also includes similar food ingredients supplied from different vendors, thus having different characteristics and nutrition facts apart from containing custom ingredient mixtures, such as sauces, of spices, characterized and evaluated accordingly, setting custom ingredient nutrition facts and flavor characteristics.

The nutrition facts can be obtained from various databases which can be considered as second database, such as but limited to, Foundation Foods, Food and Nutrient Database for Dietary Studies 2017-2018 (FNDDS 2017-2018), National Nutrient Database for Standard Reference Legacy Release (SR Legacy), USDA Global Branded Food Products Database (Branded Foods), and Experimental Foods. Each of these data types has a unique purpose and unique attributes. The ingredient nutrition values indicate per serving, among others, the amount of sodium, saturated fat, trans fat, cholesterol, sugars, iron, potassium.

The system allows formulation of a first application program incorporated in software for automatic cross correlation of the diet requirements of a typical user/consumer profile and comparing the same with the second database with appropriate room for calculation of the ratio-metric proportion of a typical customized dish to ensure customized flavor as well as nutritional value in line with the requirement of a typical user/consumer The system further deploys a process or a second application program wherein, the various ingredients of the said system evaluates the flavor profile elements per weight portion apart from the applied cooking methods and parameters such as but not limited to, temperature, moisture, heating method (induction heating, gas heating, conventional oven, microwave, air fryer). Such evaluation entailed grading the effect on the flavor profile elements vide their characterization and quantification for a typical recipe by inducing a specific flavor profile vis-à-vis the volume and quantity of the ingredients used. For example, a potato salad—American cuisine demands that it be served cold, where German potato salad is served warm to hot. Hot American potato salad is not only distasteful, but could be potentially harmful, owing to the billowy clouds of mayonnaise.

Further, the method also allows characterization of the chosen ingredient for a typical recipe/dish. Such characterization is reflected through appropriate gradation applying methods or equipment such as, but not limited to, a comparison method, by measuring instruments, using international scales or taste sensitivity tests and evaluations vide analyzing of the culinary properties such as but limited to, umami, sweetness, bitterness, salinity, sourness, spiciness, etc.

The method also ensures apt analyzing of the ingredients used for a typical recipe/dish such as but not limited to freezing, melting and boiling points, specific heat capacity, thermal conductivity, thermal diffusivity, size and thickness, deformation, density and specific gravity, refractive index, viscosity moisture levels and texture.

The method also ascertain the nutrition values per serving, among others, through assessment of the amount of sodium, saturated fat, trans fat, cholesterol, sugars, iron, potassium in an assigned recipe/dish selected by the user/consumer.

Furthermore, the system allows, the entire cross-correlation of the consumer data with the ingredient database for a typical recipe, as stated herein which can be overviewed with rooms for online input/command from the user/consumer/dietician/nutritionists concerned to interact with the recommendation of the formulation algorithm. Further, the system also allows graphical display of the change in the chemical composition for easy understanding/maneuvering by the user/consumer concerned. For example, the method will analyze the sodium levels of the salad dish recipe ingredients, and suggest to remove an adequate portion of one or more ingredients to balance the sodium levels to the original value of 500 mg, balancing the salinity levels accordingly.

The said system also allows display of suggestions vide Artificial Intelligence (AI) to add an ingredient to the recipe or increase an amount of an existing ingredient, to retain the flavor profile. For example, replacing a roasted chicken breast with tofu in an Asian dish recipe results in decrease of the dish sodium levels, since a portion of roasted chicken breast might contain 125 mg of sodium vs 25 mg of sodium in the same portion of tofu. Thus, the salinity levels of the recipe decrease accordingly by 100 mg, setting a new level for the dish flavor profile. In order to retain the flavor profile of the dish recipe, the method might suggest increasing the amount of soy sauce, being an existing ingredient of the recipe or alternatively suggest adding salt or other ingredients from the food ingredient data base.

The system further allows dynamic display of the dish recipe flavor profile during real time customization. Adding, removing or changing the amount of food ingredient, thus altering the dish recipe flavor profile and nutrition facts data, will be visually and graphically represented. Therefore, real-time feedback is provided during retention or adjustments of the flavor profile of the recipe.

The method further enables inclusion of an automation system that converts the optimal formulation recipe as finalized in the previous system for the user/individual into a machine sequence for a robotic system that allows access of each of the compound containers containing the ingredients of the approved finalized dish. These compound containers are each equipped with a digitally controlled actuator that delivers the precise volume matching of the appropriate volume of their content vide a digital measuring system to dispense the same into a common container. Such dispensing can occur either sequentially or concurrently for a typical recipe/dish to enable administers a homogenized blending of all of the ingredients. Such planned dispensing allows customizing of a typical recipe vis-à-vis the characteristic parameters of the chosen ingredients along with their typical flavor profile and nutritional compositions. For example, adding Fermented Vegetables to a salad will increase the salad recipe salinity, due to the fact that these ingredients are packed in a mixture of salt, water and spices, thus effecting, among others, the salinity parameter of the salad recipe characterization. The method in this invention receives as an input the weight or amount of the added ingredient, as per this example: fermented vegetables, analyses and graphically presents the effect of the ingredient characterization parameters on the recipe flavor profile. Following this example, a weight portion of Fermented Vegetables added to the salad recipe, containing 350 mg of sodium, indicating the salinity levels of the ingredient, is added to a salad recipe. Therefore, the salad dish recipe, originally containing 500 mg sodium, for example, now will contain 850 mg of sodium, increasing its salinity levels.

The robotic/automation process in the said system allows control of the flavor profile by adjustment of the cooking method or cooking parameters, following recipe customization. For example, chicken breast might be characterized by a deep-frying temperature of 340 F for both flavor retention and food safety considerations, while turkey breast deep frying temperature might be 275 F. Replacing a fried chicken breast for a fried turkey breast in a recipe will result in altering the deep-frying temperature accordingly. The data might be visually displayed as a real-time feedback or automatically communicated to a robotic or automated cooking apparatus.

The present disclosed subject matter may be a system, a method, and/or a computer program product. The computer program product may include a computer readable storage medium (or media) having computer readable program instructions thereon for causing a processor to carry out aspects of the present disclosed subject matter. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present disclosed subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosed subject matter. Aspects of the present disclosed subject matter are described herein with reference to flowchart illustrations and/or block diagrams of methods, apparatus (systems), and computer program products according to embodiments of the disclosed subject matter. It will be understood that each block of the flowchart illustrations and/or block diagrams, and combinations of blocks in the flowchart illustrations and/or block diagrams, can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the FIGURES illustrate the architecture, functionality, and operation of possible implementations of systems, methods, and computer program products according to various embodiments of the present disclosed subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the disclosed subject matter. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosed subject matter has been presented for purposes of illustration and description, but is not intended to be exhaustive or limited to the disclosed subject matter in the form disclosed. Many modifications and variations will be apparent to those of ordinary skill in the art without departing from the scope and spirit of the disclosed subject matter. The embodiment was chosen and described in order to best explain the principles of the disclosed subject matter and the practical application, and to enable others of ordinary skill in the art to understand the disclosed subject matter for various embodiments with various modifications as are suited to the particular use contemplated.

The invention claimed is:

1. A computer system for retaining flavor profile and nutritional values of a customized dish recipe, comprising:
    (a) a computing device having a memory;
    (b) an input device for entering information regarding recipe requirements into the memory;
    (c) a first database in the memory containing characterized food ingredients and cooking methods;

(d) a second data base of ingredients characterized by nutrition facts and flavor profile elements, including: salinity, sweetness, boiling temperature, and freezing temperature;

(e) a first application program, for execution in the computing device, for automatic cross co-relation of diet requirements of a typical consumer profile and for comparing with the second database and calculating a ratio-metric proportion of a typical customized dish to ensure customized flavor and as nutritional value required by a typical consumer;

a second application program, for over viewing a consumer recipe determined by the first application program; and g) a third application program for characterization of the characterized food ingredients.

2. The system of claim 1, wherein the third database includes information of temperature, moisture and heating methods.

3. The system of claim 2, wherein the heating methods include at least two chosen from the list including: an induction heating, a gas heating, a conventional oven, a microwave and an air fryer.

4. The system of claim 1, wherein the second application program is further configured to:

a) evaluate the flavor profile elements per weight and the effect of food ingredients, and recommending suggestions for additions, deletions, and replacement of ingredients and cooking methods as detailed in the third database, b) derive and assign the flavor profile of the customized recipe; and c) retain the dish recipe flavor by adjusting the cooking methods and parameters following recipe customization.

5. The system of claim 1, wherein the third application for characterization of the food ingredients, is configured to a) evaluate and quantify food ingredients according to culinary properties;

b) gradate the recipe based on a comparison method, measuring instruments, international taste sensitivity tests, and evaluations;

c) evaluate the physical properties of the food ingredients; and d) quantify the nutritional facts of the food ingredients obtained by the first and the second databases.

6. The system of claim 4, wherein cooking parameters are at least one chosen from the list including: a temperature, a moisture and the heating methods.

* * * * *